US005532005A

United States Patent [19]
Hedges et al.

[11] Patent Number: 5,532,005
[45] Date of Patent: Jul. 2, 1996

[54] PROCESS FOR REMOVAL OF RESIDUAL CYCLODEXTRIN

[75] Inventors: Allan Hedges; Wen Shieh, both of Crown Point; Robert Ammeraal, Worth, all of Ind.

[73] Assignee: American Maize-Products Company, Hammond, Ind.

[21] Appl. No.: 891,224

[22] Filed: May 29, 1992

[51] Int. Cl.$^6$ ........................................ A23L 1/00
[52] U.S. Cl. .................... 426/7; 426/32; 426/34; 426/45; 426/47; 426/49; 426/55
[58] Field of Search .................... 426/7, 32–34, 426/44, 45, 47, 49, 51, 52, 18, 42, 48, 55, 56, 478, 614; 435/262

[56] References Cited

U.S. PATENT DOCUMENTS

| 4,880,573 | 11/1989 | Courregelonge et al. | 426/417 |
| 4,980,180 | 12/1990 | Cully et al. | 426/47 |
| 5,342,633 | 8/1994 | Cully et al. | 426/47 |

FOREIGN PATENT DOCUMENTS

| 83413 | 3/1992 | Australia . | |
| 2657623 | 8/1991 | France . | |

OTHER PUBLICATIONS

"Cyclodextrin News" vol. 3 No. 10, Jun. 1989 Removing Undesired Components from Food.

Preliminary Product Information, Novo Enzyme Process Division, Maltogenase TM, 2 pages.

*Primary Examiner*—Leslie Wong
*Attorney, Agent, or Firm*—Lucas & Just

[57] ABSTRACT

The process entails treating a system such as a food system which contains residual cyclodextrin with both CGTase and an amylase at a temperature of 40° C. to 80° C., a pH of 4 to 6 for a time of 1 to 48 hours to hydrolyze the residual cyclodextrin. The process is especially adapted for food systems such as eggs, dairy, meat, fruit juices, coffee and tea. It is also suited for use in starch hydrolysates and protein hydrolysates. Residual cyclodextrins are contained in a system after the system has been subjected to a process wherein cyclodextrins have been employed either to remove an unwanted component or where the cyclodextrin was separated from the system.

16 Claims, No Drawings

PROCESS FOR REMOVAL OF RESIDUAL CYCLODEXTRIN

BACKGROUND OF THE INVENTION

1. Field of the Invention

The present invention relates to cyclodextrin and, more specifically, to a process for removal of residual cyclodextrin from a system. The process of the present invention is especially applicable to food systems.

2. Description of Related Art

In recent years cyclodextrin has been used to remove unwanted substances such as cholesterol from eggs or butter; caffeine from tea and coffee; phenylalanine from protein hydrolysates; and phenolic compounds, pigments and bitter components from fruit juice. Typically, this removal process entails mixing cyclodextrin with a food system such that a complex forms with the unwanted substance and the cyclodextrin, and then removing the complex from the food system.

One of the problems associated with the use of cyclodextrin to remove unwanted substances from food systems is that not all of the cyclodextrin is removed from the system when the complex is separated from the system. It is known that the complexation process is an equilibrium reaction wherein an excess amount of cyclodextrin is added to the system to push the equilibrium toward complexation. This inevitably means that a certain amount of cyclodextrin is in the uncomplexed state when the complex is removed from the system.

Another source of uncomplexed or residual cyclodextrin left behind after removal of the complex is unremoved complex. In some food systems, for example coffee, the complex is removed as a precipitate from solution. Oftentimes soluble or readily suspendable complexes are not removed from the system. In other cases, such as butter, the complexes are removed by washing the butter with water. In these instances, not all of the complexes wash away. In either case, washing or precipitation, the residual complex goes through an equilibrium reaction wherein the guest and cyclodextrin move between a complexed and uncomplexed state.

It has been suggested that the residual cyclodextrin can be removed from the food system by incubating the food system with an alpha amylase derived from the microorganisms of the group *Aspergillus niger, Aspergillus oryzae, Bacillus polymyxa, Bacillus coagulans*, Flavobacterium, or domestic hog pancreas amylase, see U.S. Pat. No. 4,980,180.

A problem associated with some alpha amylases which have been used to hydrolyze cyclodextrin is that they do not hydrolyze all cyclodextrin. Specifically, it has been found that they do not hydrolyse branched cyclodextrin and they do not hydrolyze all of the alpha cyclodextrin. There is a need for a process which completely removes all residual cyclodextrin from a food system.

SUMMARY OF THE INVENTION

It has now been discovered that all residual cyclodextrin can be removed by treating a system containing residual cyclodextrin in the presence of water with a combination of at least two separate enzymes wherein one of the enzymes is cyclodextrin glycosyl transferase (CGTase) and another enzyme is an amylase. In a preferred embodiment of the present invention, the system containing the residual cyclodextrin is also treated with a debranching enzyme in order to remove the branches from residual branched cyclodextrin. Branched cyclodextrin is more resistant to hydrolysis by the CGTase/amylase combination of the present invention than non-branched cyclodextrin. The debranching enzyme removes the branches from the branched cyclodextrin and makes the cyclodextrin more susceptible to hydrolysis by the CGTase and amylase. The addition of the debranching enzyme preferably precedes the CGTase/amylase because certain amylases such as glucoamylase and fungal alpha-amylase will work on the branch itself to reduce the branch to a glucosyl stub, which is resistant to debranching enzymes.

DESCRIPTION OF THE PREFERRED EMBODIMENTS

The step of treating the system with at least two enzymes is accomplished by adding both enzymes to the system at a pH of about 4 to about 6 and at a temperature of about 40° to about 80° C.; and maintaining the system at that temperature and pH for a period of about 1 to about 48 hours. If the system is not at the appropriate pH of 4 to 6 prior to treatment, the system is adjusted accordingly with either acid or base. Consideration of the enzymes which are to be employed and the system which is to be treated dictates the treatment conditions. Additionally, the temperature will preferably be adjusted to optimize the activity of the enzymes in the system.

Treatment of the system is carried out with conventional equipment and in the presence of water. Preferably, the enzyme is added as a separate component to the food system and mixed into the food system. Treatment is preferably conducted under agitation using conventional equipment. Alternatively, one or more of the enzymes are immobilized and the food system is passed through the immobilized enzyme.

Although the exact mechanism of the present invention is not understood, it is presumed that the CGTase causes the cyclodextrin to open and form a dextrin which the amylase then attacks and hydrolyzes. CGTase are known for their ability to form cyclodextrin from starch and starch hydrolysates. Amylases are known to hydrolyze the alpha-D-(1–4) linkage between anhydroglucose monomers while debranching enzymes are known to hydrolyze the alpha-D-(1–6) linkage between anhydroglucose monomers. Certain amylases known as glucoamylases from *Aspergillus oryzae, Aspergillus niger* and *Rhizopus nivens* are known to catalyze the hydrolysis of both the 1–4 and 1–6 linkages.

The present invention is especially suited for food systems such as egg or dairy which have been subject to a decholesterolization step wherein beta cyclodextrin has been added to complex with the cholesterol. In such a food system, the process of the present invention is employed to remove residual cyclodextrin after separation of the complexed cyclodextrin/cholesterol. The present invention works not only on cyclodextrin and branched cyclodextrin, but also on modified cyclodextrin with low degrees of substitution.

The process of the present invention has also been found to be useful in removing residual cyclodextrin from maltodextrin which is a by-product from the formation of cyclodextrin.

Suitable sources of cyclodextrin glycosyl transferase include *Bacillus macerans, Bacillus megaterium, Bacillus circulans*, and *Bacillus stearothermophilus*. Good results have been obtained with *Bacillus stearothermophilus*.

Suitable amylases include alpha-amylase, beta-amylase, and glucoamylase. The preferred amylase is a glucoamylase. Suitable sources of alpha amylases include *Bacillus licheniformis, Bacillus subtilus, Aspergillus niger*, and *Aspergillus oryzae*. Suitable beta amylases are obtained from barley malt, soy bean, and wheat. Suitable glucoamylases are obtained from *Aspergillus niger, Aspergillus oryzae, Rhizopus oryzae* and *Rhizopus nivens*. The preferred glucoamylase is obtained from *Aspergillus niger* and *Aspergillus oryzae*.

Suitable debranching enzymes are pullulanase, isoamylase and any other endo-enzymes which hydrolyze only alpha D-(1–6) glucosidic linkages of starch. Preferably, pullulanase is used as the debranching enzyme.

The amount of both CGTase and amylase added to the food system to remove residual cyclodextrins depends substantially upon the amount of residual cyclodextrins that are in the system. Preferably, about 0.005% to about 0.05% by weight CGTase is used; and about 0.005% to about 0.05% by weight amylase is used. The amount of debranching enzyme used is preferably about 0.001% to about 0.05% by weight. These weight percents are based on the weight of enzyme to weight of residual cyclodextrin.

Both CGTase and amylase must be present in the system at the same time in order to remove residual cyclodextrins. It is possible that they be added at different times so long as both are present and active in the system. Preferably, both enzymes are added to the system at the same time.

The addition of the debranching enzyme to the system is preferably done prior to the addition of the CGTase and amylase. However, the debranching enzyme can be added at the same time as the CGTase and amylase. It will be appreciated by those of skill in the art that most commercial sources of cyclodextrin contain a small portion of branched cyclodextrin.

Where necessary, the enzymes are inactivated after treatment either by adjusting the pH or by heating. Both means for inactivating the enzymes are done in a conventional manner using conventional equipment.

These and other aspects of the present invention may be more fully understood by reference to the following examples:

EXAMPLE 1

This example illustrates the present invention with a variety of amylases and compares the present invention to the use of a single enzyme, acid, or two enzymes where neither of the two enzymes are CGTase.

High performance liquid chromatography was performed to detect cyclodextrins. The detection limit of cyclodextrins is 50 ppm. The different enzymes as well as the conditions under which each set of tests were performed are listed in Table 1 below. Each system contained 20% of 15 DE starch hydrolysate with 2% residual cyclodextrins. The starch hydrolysate was adjusted to the pH indicated in Table 1 and 0.01% (w/w) of CGTase and 0.005% (w/w) of amylase were added to the solution except in runs No. 10 and No. 16 where 0.0075% (w/w) amylase was used and 0.0025% (w/w) of the debranching enzyme was used. The mixture was incubated at the temperature shown in the table with constant mixing. Enough acid was added to obtain the listed pH in run No. 1, otherwise the pH was adjusted in a conventional manner for each run.

TABLE 1

| Run | Catalyst | pH | Conditions Temp. °C. | Time (hr.) |
|---|---|---|---|---|
| 1 | Hydrochloric acid | 1.7 | 125 | ⅔ |
| 2 | CGTase | 5.0 | 80 | 24 |
| 3 | BAA, bs | 6.0 | 80 | 24 |
| 4 | BAA, bl | 6.0 | 80 | 24 |
| 5 | FAA, an | 4.8 | 50 | 24 |
| 6 | FAA, ao | 4.8 | 50 | 24 |
| 7 | GA, an | 4.8 | 50 | 24 |
| 8 | GA, ao | 4.8 | 50 | 24 |
| 9 | Mase | 6.0 | 60 | 24 |
| 10 | Pase/GA, an | 4.8 | 50 | 24 |
| 11 | CGTase/BAA, bl | 5.5 | 80 | 24 |
| 12 | CGTase/FAA, an | 4.8 | 50 | 24 |
| 13 | CGTase/FAA, ao | 4.8 | 50 | 24 |
| 14 | CGTase/GA, an | 4.8 | 50 | 24 |
| 15 | CGTase/GA, ao | 4.8 | 50 | 24 |
| 16 | CGTase/Pase/GA, an | 4.8 | 50 | 24 |

The enzymes and their sources as abbreviated in Table 1 above are as follows:

CGTase=cyclodextrin glycosyl transferase from *Bacillus stearothermophilus*.

BAA, bs=bacterial alpha amylase from *Bacillus subtilus*.

BAA, bl=bacterial alpha amylase from *Bacillus licheniformis*.

FAA, an=fungal alpha amylase from *Aspergillus niger*.

FAA, ao=fungal alpha amylase from *Aspergillus oryzae*.

GA, an=glucoamylase from *Aspergillus niger*.

GA, ao=glucoamylase from *Aspergillus oryzae*.

Mase=a form of maltogenic alpha amylase obtained from *Bacillus subtilus* and sold by Novo Enzyme Process Division, Denmark, under the name MALTOGENASE.

Pase=Pullulanase from *Bacillus sp*.

After treating each of the starch hydrolysates, high performance liquid chromatography was used to determine the amount of cyclodextrin remaining in solution. From these tests it was observed that cyclodextrin still remained after runs 1–10. It was specifically noted that alpha cyclodextrin was present after runs 5, 6 and 10. No cyclodextrins were detected after runs 11–16.

EXAMPLE 2

This example illustrates the present invention to remove residual cyclodextrin from decaffeinated coffee.

Ten (10) grams of beta-cyclodextrin were added to one hundred (100) milliliters of coffee solution. After treatment for one hour at 60° C. the solution was allowed to cool to room temperature and a complex of caffeine and cyclodextrin was filtered from the solution. Next, the pH of the filtrate, decaffeinated coffee solution, was adjusted to 5 and high performance liquid chromatography was performed to determine that the filtrate contained 3.3% by weight beta cyclodextrin. The detection limit on the high performance liquid chromatography for cyclodextrin was 50 ppm. Then, the filtrate was treated as described in Example 1 with the enzymes as listed in Table 2 below.

TABLE 2

| Run | Catalyst | pH | Conditions Temp. °C. | Time (hr.) |
|---|---|---|---|---|
| 1 | CGTase/BAA, bl | 5.0 | 80 | 24 |
| 2 | CGTase/FAA, an | 5.0 | 50 | 24 |
| 3 | CGTase/FAA, ao | 5.0 | 50 | 24 |
| 4 | CGTase/Mase | 5.0 | 50 | 24 |

TABLE 2-continued

| Run | Catalyst | pH | Conditions Temp. °C. | Time (hr.) |
|---|---|---|---|---|
| 5 | CGTase/Pase/GA, an | 5.0 | 50 | 24 |

After each run, it was noted that no cyclodextrin was detected.

EXAMPLE 3

This example illustrates the use of the present invention in a pharmaceutical system.

Microbial conversion of hydrocortisone to prednisolone was done using a beta cyclodextrin complex of the hydrocortisone to solubilize the hydrocortisone and accelerate the rate of the reaction. The prednisolone complex was recovered from the reaction. In order to prepare a product suitable for injection, the decomplexed and isolated prednisolone was suspended in water and treated with a mixture of CGTase and amylase to remove any traces of beta cyclodextrin.

EXAMPLE 4

This example illustrates the use of the present invention in an industrial system, a cleaning solution.

Beta cyclodextrin was used to provide an enrichment of para xylene to produce a special cleaning solvent. Removal of the cyclodextrin was incomplete and a residue was left on the component being cleaned. The small residue was interfering with the operation of the component.

The para xylene solvent was stirred in water containing a mixture of CGTase and amylase to hydrolyze residual cyclodextrins. The hydrolysis products had no affinity for the para xylene and remained in the aqueous phase. The enzyme treated para xylene left no interfering residue on the component after cleaning.

It will be understood that the claims are intended to cover all changes and modifications of the preferred embodiment of the invention herein chosen for the purpose of illustration which do not constitute a departure from the spirit and scope of the invention.

What is claimed is:

1. A process for removing uncomplexed, residual cyclodextrin from a system which has been subjected to a step wherein a complex of cyclodextrin has been removed and which contains other material besides uncomplexed, residual cyclodextrin and water, said process comprising the steps of treating said system containing uncomplexed, residual cyclodextrin and water with a CGTase and an amylase simultaneously at a pH of about 4 to about 6, a temperature of about 40° to about 80° C., for a period of time of about 1 to about 48 hours to hydrolyze the uncomplexed, residual cyclodextrin.

2. The process of claim 1 wherein the amylase is selected from the group consisting of alpha amylase, beta amylase and glucoamylase.

3. The process of claim 1 or 2 wherein the system is a food system selected from the group consisting of eggs, dairy, meat, suet, lard, fruit juice, coffee and tea.

4. The process of claim 1 or 2 wherein the system is a starch hydrolysate or a protein hydrolysate.

5. The process of claim 1 or 2 wherein the amylase is a bacterial alpha amylase, a fungal alpha amylase or a glucoamylase.

6. A purification process for a system which has been previously treated with a cyclodextrin to form a complex with a component in said system and said system with said complex was then subjected to a separation step wherein said complex has been removed from said system, said system now comprising uncomplexed residual cyclodextrin, water and other components besides said uncomplexed cyclodextrin and water, said purification process comprising the steps of treating said system with CGTase and an amylase simultaneously at a pH of about 4 to about 6, a temperature of about 40° to about 80° C., for a period of time of about 1 to about 48 hours to hydrolyze the residual cyclodextrin.

7. The process of claim 6 wherein the amylase is selected from the group consisting of alpha amylase, beta amylase and glucoamylase.

8. The process of claim 6 or 7 wherein the system is a food system selected from the group consisting of eggs, dairy, meat, suet, lard, fruit juice, coffee and tea.

9. A process for removing uncomplexed, residual cyclodextrin from a system which has been subjected to a step wherein a complex of cyclodextrin has been removed and which contains other material besides uncomplexed, residual cyclodextrin and water, said process comprising the successive steps of: (a) treating said system containing uncomplexed, residual cyclodextrin and water with a debranching enzyme at a pH of about 4 to about 6, at a temperature of about 40° C. to about 80° C. and for a period of time of about 1 to about 48 hours; and subsequently (b) treating said system with a CGTase and an amylase simultaneously at a pH of about 4 to about 6, a temperature of about 40° to about 80° C., for a period of time of about 1 to about 48 hours to hydrolyze the uncomplexed, residual cyclodextrin.

10. A process for removing uncomplexed, residual cyclodextrin from a system which has been subjected to a step wherein a complex of cyclodextrin has been removed and which contains other material besides uncomplexed, residual cyclodextrin and water, said process comprising the steps of treating said system containing uncomplexed, residual cyclodextrin and water with a CGTase, an amylase, and a debranching enzyme simultaneously at a pH of about 4 to about 6, at a temperature of about 40° C. to about 80° C. and for a period of time of about 1 to about 48 hours to hydrolyze the uncomplexed, residual cyclodextrin.

11. A purification process for a system which has been previously treated with a cyclodextrin to form a complex with a component in said system and said system with said complex was then subjected to a separation step wherein said complex has been removed from said system, said system now comprising uncomplexed residual cyclodextrin, water and other components besides said uncomplexed cyclodextrin and water, said purification process comprising the steps of: (a) treating said system with a debranching enzyme at a pH of about 4 to about 6, at a temperature of about 40° to about 80° C. and for a period of time of about 1 to about 48 hours; and subsequently (b) treating said system with CGTase and an amylase simultaneously at a pH of about 4 to about 6, a temperature of about 40° to about 80° C., for a period of time of about 1 to about 48 hours to hydrolyze the residual cyclodextrin.

12. The process of claim 9, 10 or 11 wherein the amylase is selected from the group consisting of alpha amylase, beta amylase and glucoamylase.

13. The process of claim 9, 10 or 11 wherein the amylase is a bacterial alpha amylase, a fungal alpha amylase, or a glucoamylase.

14. The process of claim 9, 10 or 11 wherein the amylase is selected from the group consisting of alpha amylase, beta amylase and glucoamylase; and the system is a food system selected from the group consisting of eggs, dairy, meat, suet, lard, fruit juice, coffee and tea.

15. The process of claim 9, 10 or 11 wherein the system is a starch hydrolysate or a protein hydrolysate.

16. The process of claim 9, 10 or 11 wherein the amylase is selected from the group consisting of alpha amylase, beta amylase and glucoamylase; and the system is a starch hydrolysate or a protein hydrolysate.

* * * * *